(12) United States Patent
Finkman et al.

(10) Patent No.: US 9,138,134 B2
(45) Date of Patent: Sep. 22, 2015

(54) ENDOSCOPE WITH AN IMPROVED WORKING CHANNEL

(71) Applicant: C2Cure Inc., Wilmington, DE (US)

(72) Inventors: Shai Finkman, Haifa (IL); Doron Adler, Haifa (IL)

(73) Assignee: GYRUS ACMI, INC., Southborough, MA (US)

( * ) Notice: Subject to any disclaimer, the term of this patent is extended or adjusted under 35 U.S.C. 154(b) by 0 days.

(21) Appl. No.: 13/895,821

(22) Filed: May 16, 2013

(65) Prior Publication Data

US 2013/0253270 A1    Sep. 26, 2013

Related U.S. Application Data

(63) Continuation of application No. 12/637,513, filed on Dec. 14, 2009, now Pat. No. 8,465,421.

(51) Int. Cl.
*A61B 1/12* (2006.01)
*A61B 1/015* (2006.01)
*A61B 1/00* (2006.01)
*A61B 1/313* (2006.01)
*A61B 1/018* (2006.01)
*A61B 1/04* (2006.01)
*A61B 1/307* (2006.01)

(52) U.S. Cl.
CPC ............. *A61B 1/015* (2013.01); *A61B 1/00091* (2013.01); *A61B 1/12* (2013.01); *A61B 1/3137* (2013.01); *A61B 1/018* (2013.01); *A61B 1/04* (2013.01); *A61B 1/307* (2013.01)

(58) Field of Classification Search
USPC .................................................. 600/156–159
See application file for complete search history.

(56) References Cited

U.S. PATENT DOCUMENTS

| 3,835,842 A | 9/1974 | Iglesias |
| 3,850,175 A | 11/1974 | Iglesias |
| 4,092,003 A | 5/1978 | Ikeuchi |
| 4,132,227 A | 1/1979 | Ibe |
| 4,349,014 A * | 9/1982 | Takamatsu ..................... 600/109 |

(Continued)

FOREIGN PATENT DOCUMENTS

| JP | 56-113501 | 9/1981 |
| JP | 4290013 | 4/2009 |

(Continued)

OTHER PUBLICATIONS

Office Action issued by United States Patent and Trademark Office for U.S. Appl. No. 11/560,796 dated Jul. 14, 2009; 9 pages.

(Continued)

*Primary Examiner* — Matthew J Kasztejna
(74) *Attorney, Agent, or Firm* — The Dobrusin Law Firm, P.C.

(57) ABSTRACT

A medical device includes an insertion tube, having a proximal end and a distal end, which is configured for insertion into a body cavity of a subject. An optical assembly is contained in the distal end and configured to form an image of a target region in the body cavity. A working channel passes through the insertion tube and is configured to convey a fluid from the proximal to the distal end. The working channel has a segment adjacent to the distal end that is narrowed so as to cause the fluid to exit the working channel into the target region in a diverging cone.

9 Claims, 3 Drawing Sheets

(56) References Cited

U.S. PATENT DOCUMENTS

| | | | |
|---|---|---|---|
| 4,423,727 A * | 1/1984 | Widran et al. | 606/46 |
| 4,448,188 A | 5/1984 | Loeb | |
| 4,576,146 A | 3/1986 | Kawazoe et al. | |
| 4,602,281 A | 7/1986 | Nagasaki et al. | |
| 4,611,888 A | 9/1986 | Prenovitz et al. | |
| 4,739,766 A | 4/1988 | Riederer | |
| 4,827,907 A | 5/1989 | Tashiro | |
| 4,934,339 A | 6/1990 | Kato | |
| 4,959,058 A | 9/1990 | Michelson | |
| 4,998,972 A | 3/1991 | Chin et al. | |
| 5,010,875 A | 4/1991 | Kato | |
| 5,106,022 A | 4/1992 | Pook | |
| 5,191,878 A * | 3/1993 | Iida et al. | 600/157 |
| 5,269,289 A * | 12/1993 | Takehana et al. | 600/109 |
| 5,287,845 A | 2/1994 | Faul et al. | |
| 5,320,091 A | 6/1994 | Grossi et al. | |
| 5,486,155 A | 1/1996 | Muller et al. | |
| 5,509,892 A | 4/1996 | Bonnet | |
| 5,618,001 A | 4/1997 | Del Gaone et al. | |
| 5,688,222 A | 11/1997 | Hluchy et al. | |
| 5,725,477 A | 3/1998 | Yasui et al. | |
| 5,807,240 A | 9/1998 | Muller et al. | |
| 5,836,909 A | 11/1998 | Cosmescu | |
| 5,855,549 A | 1/1999 | Newman | |
| 5,857,962 A | 1/1999 | Bracci et al. | |
| 6,042,026 A | 3/2000 | Buehler, II | |
| 6,086,542 A | 7/2000 | Glowa et al. | |
| 6,132,369 A | 10/2000 | Takahashi | |
| 6,159,160 A | 12/2000 | Hsei et al. | |
| 6,176,847 B1 | 1/2001 | Humphreys, Jr. et al. | |
| 6,178,346 B1 | 1/2001 | Amundson et al. | |
| 6,309,347 B1 * | 10/2001 | Takahashi et al. | 600/159 |
| 6,315,712 B1 | 11/2001 | Rovegno | |
| 6,354,992 B1 | 3/2002 | Kato | |
| 6,358,200 B1 | 3/2002 | Grossi | |
| 6,447,446 B1 | 9/2002 | Smith et al. | |
| 6,692,430 B2 | 2/2004 | Adler | |
| 6,712,759 B2 | 3/2004 | Muller | |
| 6,860,438 B1 | 3/2005 | Huang | |
| 6,881,188 B2 | 4/2005 | Furuya et al. | |
| 7,051,524 B1 | 5/2006 | Kraft | |
| 7,479,106 B2 | 1/2009 | Banik et al. | |
| 7,588,535 B2 | 9/2009 | Adler et al. | |
| 7,758,499 B2 | 7/2010 | Adler | |
| 7,892,167 B2 | 2/2011 | Francisco et al. | |
| 2001/0004692 A1 | 6/2001 | Kidooka et al. | |
| 2002/0058859 A1 | 5/2002 | Brommersma | |
| 2004/0147806 A1 | 7/2004 | Adler | |
| 2004/0204671 A1 * | 10/2004 | Stubbs et al. | 604/26 |
| 2006/0047184 A1 | 3/2006 | Banik et al. | |
| 2006/0069306 A1 | 3/2006 | Banik et al. | |
| 2007/0100241 A1 | 5/2007 | Adler | |
| 2007/0278331 A1 | 12/2007 | Hansson | |
| 2007/0290073 A1 | 12/2007 | Peterson et al. | |
| 2009/0318798 A1 | 12/2009 | Singh et al. | |

FOREIGN PATENT DOCUMENTS

| | | |
|---|---|---|
| WO | 03053226 | 7/2003 |
| WO | 03057020 | 7/2003 |
| WO | 03098913 | 11/2003 |
| WO | 2009/095915 | 8/2009 |

OTHER PUBLICATIONS

Final Office Action issued by United States Patent and Trademark Office for U.S. Appl. No. 11/560,796 dated Feb. 3, 2010; 11 pages.
Office Action issued by United States Patent and Trademark Office for U.S. Appl. No. 10/041,645 dated Jan. 7, 2002; 8 pages.
Final Office Action issued by United States Patent and Trademark Office for U.S. Appl. No. 10/041,645 dated Aug. 8, 2003; 8 pages.
Notice of Allowance and Notice of Allowability issued by United States Patent and Trademark Office for U.S. Appl. No. 10/041,645 dated Oct. 7, 2003; 4 pages.
PCT International Search Report dated Jun. 5, 2003 for International Patent Application No. PCT/US03/00359; 5 pages.
PCT International Written Opinion dated Jan. 16, 2004 for International Patent Application No. PCT/US03/00359; 5 pages.
PCT International Preliminary Report dated Oct. 12, 2004 for International Patent Application No. PCT/US03/00359; 7 pages.
Examination Report issued by European Patent Office for European Patent Application No. 03729358.6 dated Dec. 11, 2006; 4 pages.
Examination Report issued by European Patent Office for European Patent Application No. 03729358.6 dated Apr. 14, 2008; 6 pages.
Final Examination Report issued ny European Patent Office for European Patent Application No. 03729358.6 dated Dec. 1, 2009; 7 pages.
English Translation of Office Action issued by the Japanese Pantent Office for Japanese Patent Application No. 2003-557388, dated Apr. 22, 2008; 4 pages.
H.J Sheen, W.J. Chen and J.S. WU; (Abstract only) Flow patterns for an Annular flow over an axisymmetric sudden expansion; Journal of fluid Mechanics (1997), 350:177-188 Cambridge University Press Copyright 1997 Cambridge University Press.
http://www.spray.co.za/tag/solid-stream-nozzle- Spraying Systems Co. Experts in Spray Technology- mhtml:file ://V/Projects/Patents/Flow improvement/Referenced/Section2/ Ref int 1, Solid; Monitor Engineering 2009 (4 pages).
http://www.fluidproducts.com/typesoffullcones.htm Air Knofe Drying systems- 3 Types of Full Cone Spray Nozzles T.P.S, Inc. Blairstown NJ 07825; 2001-2008 T.P.S, Inc. 1 page.
http://www.msubbu.in/fm/Unit-III/VenturiMeter.htm-VenturiMater-mhtml:file;//V:/Projects/Patnets/Flowimprovement/References/Section2/Ref int3, Ventur: 2 pages.
M.Buscaeini: M. Conlin. Update on Flexible Ureteroscopy. Urologia Internationalis. 80:1-7, 2008 S. Karger AG, Basel (7 pages).
E.K. Naumenko; Influence of Erythrocyte Aggregation on the Scattering Properties of Blood; Journal of Applied Spectroscopy, vol. 70, No. 3, 2003 (1 page).
Gyrus ACMI-DUR-Digital Invisio-Flexible Ureteroscope/Choledochoscope Operations and Technical Manual ACMI Corporation; 136 Turnpike Road- Southborough, MA 01772-2104 USA 2006 ACMI Corporation, All rights Reserved (20 Pages).
S. Mader, Understanding Human Anatomy & Physiology, fifth edition. The McGraw-Hill Companies, p. 325, 2004.
P. Singh, et al. Minimal invasive treatment of ureteropelvic junction obstruction in low volume pelvis: A comparative studu endopyelotomy and laparoscopic nondismembered pyeloplasty. Indian Journal of Urology, 25(1): 68-71, 2009 (4 pages).
Cristiana-Gabriela Popwscu-Ungueanu, Amelitta Legendi, Mircea Degeratu, Bardescu; Experimental Determinations with Sand-Blasting mobile Unit having free Diphase Jet; Annals of the Oradea University. Fascicle of Management and Technological Engineering, vol. VII (XVII)2008 (7 pages).
A Baylar, PhD. MSc, F. Ozkar; PhD, MSc; Influence of venture cone angles on jet aerationsystems; Water Management 158; Mar. 2005 Issue WNI; pp. 9-16.
http;//www.sambasensors.com/attachments/Samba%20in%20 Urodynamics.pdf: Samba Sensors, Novel Micro Pressure catheter for urodynamic investigations; Samba Sensors AB Forsta Langgatan 26; S-413 28 Gotebor Sweden; 2008 Samba Sensors.
PCT International Search Report and Written Opinion dated Jul. 20, 2011, for International Application No. PCT/US2010/058232; 15 pages total.
Andre Roggan, Moritz Friebel, Klaus Dorschel, Andreas Hakn, and Gergard Muller; Optical Properties of Circulating Human blood in the wavelength Range 400-2500 NM; Journal of Biomedical Optics 2 (1), 36-46 (Jan. 1999).
PCT International Search Report and the Written Opinion of the International Searching Authority for the International Application No. PCT/US2011/037978; dated Sep. 22, 2011 (12 pages total).

* cited by examiner

ENDOSCOPE WITH AN IMPROVED WORKING CHANNEL

CLAIM OF PRIORITY

This application is a continuation of Ser. No. 12/637,513 filed on Dec. 14, 2009, and claims priority therefrom incorporated herein by reference.

BACKGROUND

The present inventive subject matter relates generally to medical instruments, and specifically to endoscopic devices and methods.

Endoscopes commonly contain a working channel, which may be used to introduce specially-designed diagnostic and therapeutic instruments into the area under view inside the body. In some systems, the working channel may be connected to a pump outside the body and used for suction or fluid delivery (irrigation) to the area of the distal tip of the endoscope. For example, a clear fluid, such as saline solution, may be injected through the working channel in order to clean the endoscope viewing window and/or clear debris from the area under view.

PCT International Publication WO 03/053226, whose disclosure is incorporated herein by reference, describes an endoscope for use in intravascular photographic imaging. In one embodiment, a fluid is injected via an open channel in order to dilute the blood in the vicinity of a target region to be imaged. A control unit controls the amount of injected fluid according to whether the imaging data meets a predetermined threshold of resolution or other measure of quality.

U.S. Patent Application Publication 2001/0004692, whose disclosure is incorporated herein by reference, describes an endoscopic spraying instrument, which can spray liquid uniformly over all directions. A rotatingly-guiding groove at the leading end of a liquid-supplying tube is rotated about an central axis within a liquid-rotating chamber at the leading end. The liquid is discharged forwardly from an ejection hole formed in the wall of the liquid-rotating chamber. An annular, protruded wall is spaced outwardly from the outer periphery of the ejection hole.

SUMMARY

Embodiments of the present inventive subject matter that are described hereinbelow provide devices and methods for controlling and efficiently exploiting the flow of fluid through an endoscope working channel.

There is therefore provided, in accordance with an embodiment of the present inventive subject matter, a medical device, including an insertion tube, having a proximal end and a distal end, which is configured for insertion into a body cavity of a subject. An optical assembly is contained in the distal end and is configured to form an image of a target region in the body cavity. A working channel passes through the insertion tube and is configured to convey a fluid from the proximal to the distal end, and has a segment adjacent to the distal end that is narrowed so as to cause the fluid to exit the working channel into the target region in a diverging cone.

In a disclosed embodiment, the working channel includes a converging segment proximal to the narrowed segment and a diverging segment distal to the narrowed segment, such that the converging, narrowed and diverging segments together define a Venturi tube. Additionally or alternatively, the working channel has an inner surface in which spiral grooves are formed so as to cause a vortical flow of the fluid through the narrowed segment.

In some embodiments, the working channel is configured to accommodate a tool, which is passed through the working channel into the target region while the fluid irrigates the target region. The tool may include an obstructing element, which is positioned at the distal end of the working channel so as to narrow the segment adjacent to the distal end.

Additionally or alternatively, the apparatus includes a fluid sensor, which is configured to measure a characteristic of a flow of the fluid through the working channel.

There is also provided, in accordance with an embodiment of the present inventive subject matter, medical apparatus, including an endoscope, which includes an insertion tube, having a proximal end and a distal end, which is configured for insertion into a body cavity of a subject. The endoscope contains a working channel, which is configured to convey a fluid from the proximal end to a target region in the body cavity adjacent to the distal end. A fluid sensor is configured to measure a characteristic of a flow of the fluid through the working channel. A control unit is configured to regulate the flow of the fluid through the working channel responsively to the measured characteristic.

In disclosed embodiments, the endoscope includes an optical assembly contained in the distal end and configured to form an image of the target region, and the control unit is configured to process the image and to regulate the flow of the fluid through the working channel responsively to a quality of the image. Typically, the control unit is configured to set the flow automatically, responsively to the measured characteristic and the quality of the image, so as to maximize a contrast of the image while minimizing a rate of the flow, within respective, predetermined upper and lower limits of the rate and contrast.

In one embodiment, the fluid sensor is contained in the distal end of the endoscope. In an alternative embodiment, the fluid sensor is coupled to the working channel outside the proximal end of the endoscope. The fluid sensor may include a pressure sensor, or it may be configured to measure a rate of flow of the fluid through the working channel.

There is additionally provided, in accordance with an embodiment of the present inventive subject matter, a method for medical treatment, including providing an endoscope having a distal end for insertion into a body cavity of a subject, the distal end containing an optical assembly configured to form an image of a target region in the body cavity. A fluid is conveyed through a working channel, which passes from a proximal end of the endoscope to the distal end and has a segment adjacent to the distal end that is narrowed so as to cause the fluid to exit the working channel into the target region in a diverging cone.

There is further provided, in accordance with an embodiment of the present inventive subject matter, a method for medical treatment, including providing an endoscope having a distal end for insertion into a body cavity of a subject and containing a working channel for conveying a fluid from a proximal end of the endoscope to a target region in the body cavity adjacent to the distal end. A characteristic of a flow of the fluid through the working channel is measured, and the flow of the fluid through the working channel is regulated responsively to the measured characteristic.

The present inventive subject matter will be more fully understood from the following detailed description of the embodiments thereof, taken together with the drawings in which:

DETAILED DESCRIPTION

In many endoscopic procedures, the target region that is viewed by the endoscope is irrigated to remove blood and debris so as to give the operator (typically a physician) a clear picture of the region. This irrigation is carried out through a working channel of the endoscope, which may also be used (even simultaneously) for insertion of endoscopic tools into the target region. It is desirable that the fluid exit the working channel in a wide, uniform cone in order to effectively irrigate the entire target region.

Some embodiments of the present inventive subject matter, as described hereinbelow, address the need for effective irrigation, and provide solutions that are effective even when an endoscopic tool is also present in the working channel. In these embodiments, the working channel has a segment adjacent to the distal end of the endoscope that is narrowed so as to cause the fluid to spread from the working channel into the target region in a diverging cone. In some embodiments, the working channel comprises a converging segment proximal to the narrowed segment and a diverging segment distal to the narrowed segment, thus defining a Venturi tube. In other embodiments, the tool comprises an obstructing element, such as a collar, which is positioned at the distal end of the working channel so as to narrow the adjacent segment of the working channel. The inner surface of the working channel may also be configured to cause a vortical flow of the fluid (i.e., swirling around the axis of the channel) through the narrowed segment of the working channel, which further enhances the spread of the exiting fluid.

Excessive irrigation is undesirable, as it can overload the patient's body with fluid. Therefore, in some embodiments of the present inventive subject matter, a control unit regulates the flow of the irrigation fluid so as to use the minimal amount of fluid necessary to give images of sufficient quality. For this purpose a fluid sensor measures a characteristic of the fluid flow through the working channel, such as the pressure or flow rate. The control unit monitors this flow characteristic, as well as the quality of the image (as expressed, for example, by a measure of image contrast), and adaptively increases and decreases the fluid flow as required, within predetermined bounds, to reach the desired balance between fluid flow and image quality. The control unit may carry out these functions automatically, without active involvement of the operator.

Figure 1:
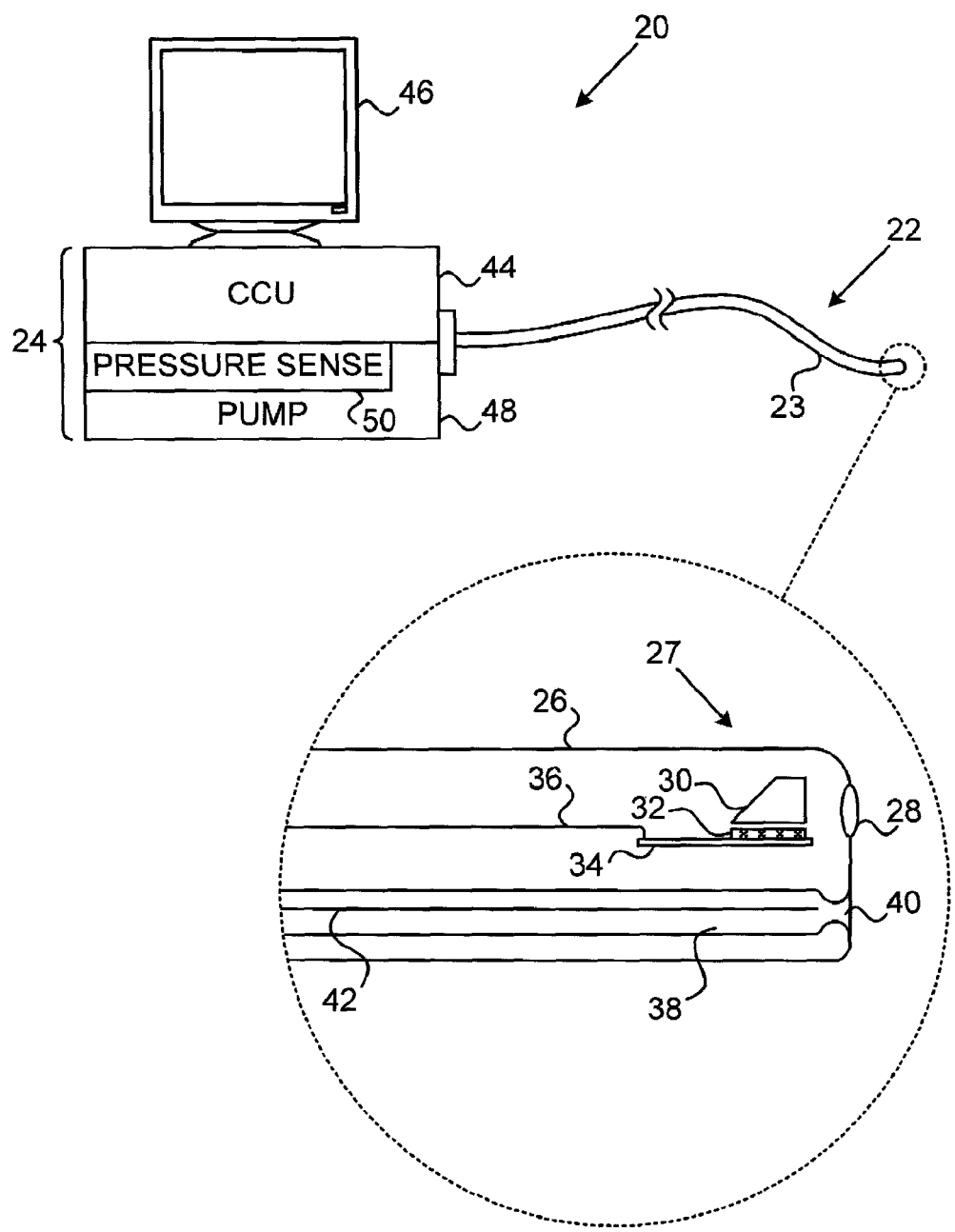
FIG. 1 is a schematic side view of a system for endoscopy, in accordance with an embodiment of the present inventive subject matter.

FIG. 1 is a schematic side view of a system 20 for endoscopy, in accordance with an embodiment of the present inventive subject matter. The system comprises an endoscope 22, which is connected at its proximal end to a control console 24. The endoscope comprises a flexible insertion tube 23, having a distal end 26 (shown in a detailed sectional view in the inset in FIG. 1) for insertion into a body cavity. In the present embodiment, it will be assumed that endoscope 22 is a ureteroscope, which is designed for insertion through the patient's urethra, bladder and ureter to the renal pelvis. This sort of endoscope is generally restricted to a small diameter, typically no greater than 3 mm, which accordingly limits the number and size of working channels and other functional components that can be accommodated in the endoscope. Alternatively, the principles of the present inventive subject matter may be applied in endoscopes of other types.

Distal end 26 contains an optical assembly 27 of a type that is described, for example, in PCT International Publication WO 03/098913, whose disclosure is incorporated herein by reference. Briefly, an optical objective 28 collects light from a target region outside the distal end and focuses the light via a turning mirror 30 (shown here in the form of a prism) onto an image sensor 32, whose focal plane is parallel to the longitudinal axis of insertion tube 23. The image sensor is mounted on a circuit board 34, which is connected by wires 36 running through the endoscope to console 24. Distal end 26 typically also contains one or more light sources (not shown) for illuminating the target region.

This optical assembly is shown in FIG. 1 by way of example, and the principles of the present inventive subject matter may similarly be applied in conjunction with other types of endoscopic optical assemblies that are known in the art. For example, the focal plane of the image sensor may be perpendicular to the axis of the insertion tube, as in most endoscopes that are known in the art. As another example, the optical assembly in the distal end of the endoscope may comprise an image guide, such as a fiberoptic bundle, which conveys the image captured by the optical objective to a camera head at the proximal end of the endoscope. The endoscope itself may be rigid, rather than flexible as shown here.

A working channel 38 passes through insertion tube 23 from the proximal end (at console 24) to distal end 26. This working channel may be used both to pass endoscopic tools through endoscope 22, to operate in the target region, and to irrigate the target region. For the latter purpose, the working channel ends in a nozzle 40 at the distal end. The nozzle contains a narrowed segment adjacent to the distal end, which causes the irrigation fluid to exit the working channel into the target region in a diverging cone, as described in greater detail hereinbelow. A pump 48 in console 24 drives fluid through the working channel at a controllable rate.

Console 24 comprises a camera control unit (CCU) 44, which receives and processes the signals carried from optical assembly 27 over wires 36 in order to generate output images of the target region. The images may be displayed on a screen 46. The CCU may also extract indicators of image quality, such as a measure of the image contrast, and may use these indicators in controlling the flow of the irrigation fluid driven by pump 48, as described in detail hereinbelow. CCU 44 typically comprises a general-purpose or embedded microprocessor, with input and output circuits for communicating with the other elements of system 20. CCU devices that are known in the art may be used for this purpose, with the possible addition of input/output connections for pressure measurement and flow control, as well as suitable software to carry out the functions that are described hereinbelow. Alternatively, these functions may be performed by dedicated or programmable hardware logic.

Endoscope 22 contains a fluid sensor 42, which measures a characteristic of the fluid flowing through working channel 38. For example, sensor 42 may be a miniature pressure sensor, which measures the fluid pressure inside the working channel (as shown in FIG. 1) or in the target region outside the distal end of the endoscope. One type of pressure sensor that may be used for this purpose is a Samba MicroC 420 UD transducer (produced by Samba Sensors AB, Goteborg, Sweden), comprising an optical fiber with a pressure-sensitive optical cavity at its distal tip. The sensor may be deployed in the working cavity as shown in FIG. 1, or it may alternatively be integrated within the body of insertion tube 23. As long as the flow characteristics of working channel 38 are known, the pressure measurement gives a reliable indicator of the flow rate.

Alternatively, sensor 42 may measure flow rate by other means. For example, sensor 42 may comprise a heating element and a temperature sensor, which indicates the rate of flow based on the rate at which the fluid flowing through the working channel cools the heating element. Alternatively or additionally, a pressure sensor 50 or other flow sensing element may be coupled to the working channel outside the proximal end of endoscope 22. For example, sensor 50 may be integrated with console 24, as shown below in FIG. 4.

Figure 2:
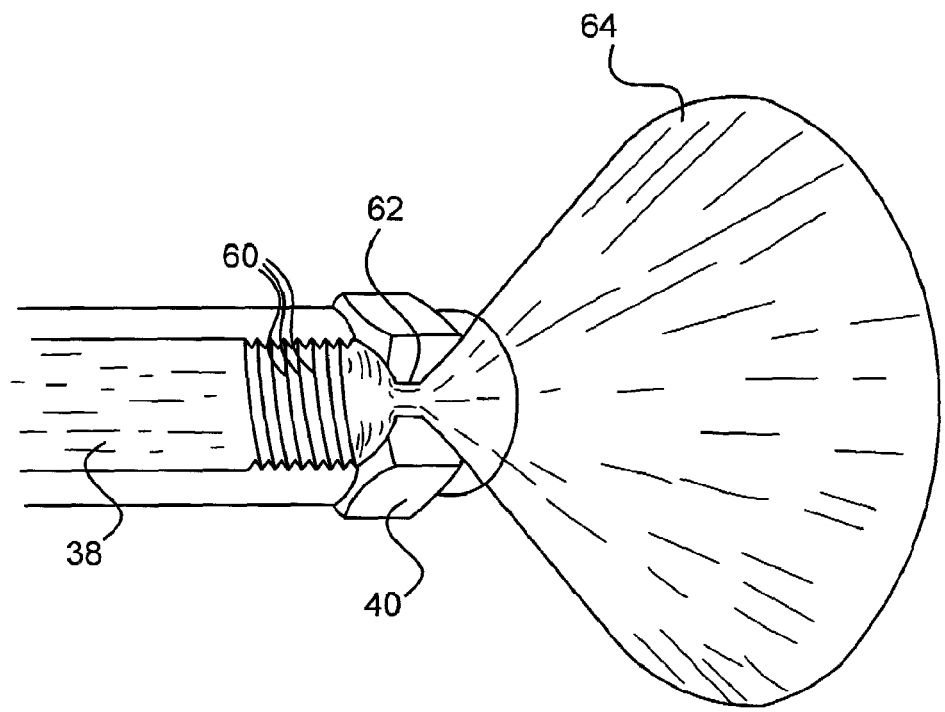
FIG. 2 is a schematic cutaway view of a nozzle used in an endoscope, in accordance with an embodiment of the present inventive subject matter.

FIG. 2 is a schematic cutaway view showing details of nozzle 40, in accordance with an embodiment of the present inventive subject matter. The nozzle has the form of a Venturi tube, with a narrow waist 62 preceded by a converging segment (to the left in the figures) and followed by a diverging segment (to the right), so that the irrigation fluid is emitted from the nozzle to form an expanding cone 64. A variety of types of Venturi tubes, as well as methods for designing such tubes, are known in the art. Representative examples are presented in U.S. Pat. Nos. 4,092,003; 5,618,001; 5,106,022; 6,042,026; 6,860,438; and 7,051,524, as well as in U.S. Patent Application Publications 2001/0004692; 2007/0278331; and 2007/0290073, all of whose disclosures are incorporated herein by reference.

In the present case, the inventors have found that an effective conical spread of the emitted fluid can be achieved using the following parameters, wherein dimensions are relative to the diameter of waist 62, which is identified as "X":
Length of waist X–5.5X.
Convergence angle of converging segment –21±2°.
Diameter of converging segment –2X–2.5X.
Divergence angle of diverging segment –5–15°.
Diameter of diverging segment X–3X.
The optimal dimensions may be found in each case based on the specific geometrical constraints of the endoscope, using techniques described in the above-mentioned references.

Furthermore, to broaden the spread of the fluid exiting nozzle 40 in cone 64, the nozzle may contain spiral grooves 60 within its inner surface. These grooves introduce a vortical component (swirling motion) in the fluid flow, which enhances the fluid spread without significantly obstructing channel 38.

Figure 3:
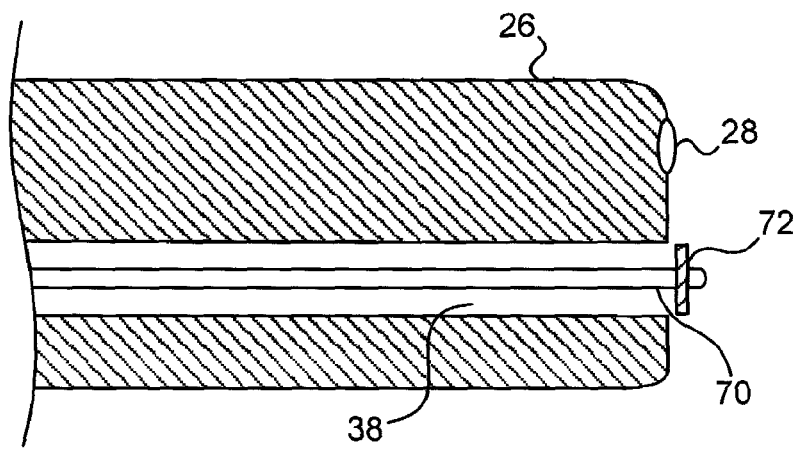
FIG. 3 is a schematic sectional view of the distal end of an endoscope, in accordance with another embodiment of the present inventive subject matter.

FIG. 3 is a schematic sectional view of distal end 26 of an endoscope, in accordance with an embodiment of the present inventive subject matter. In this embodiment, a tool 70, such as an optical fiber for delivering laser radiation, is inserted through working channel 38. The tool has an obstructing element, in the form of a collar 72, which significantly narrows the distal segment of the working channel at its outlet. The collar may be integrally formed as part of tool 70, or it may be fitted onto the tool as required. The obstructing element has the effect of spreading the flow of the irrigation fluid into a cone, whose angular spread may be controlled by advancing and retracting tool 70. The particular size and shape of collar 72 are shown in FIG. 3 solely by way of example, and other sizes and shapes may be used, as well.

Figure 4:
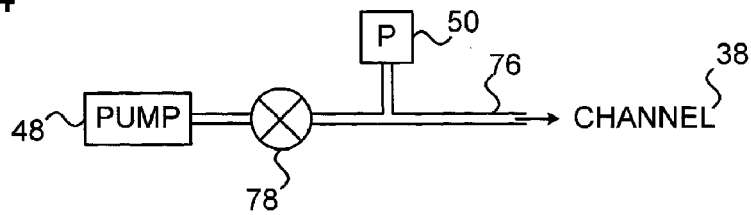
FIG. 4 is a block diagram that schematically illustrates components used for flow control in a system for endoscopy, in accordance with an embodiment of the present inventive subject matter.

FIG. 4 is a block diagram that schematically illustrates components that may be used for flow control in system 20, in accordance with an alternative embodiment of the present inventive subject matter. In this example, pump 48 and pressure sensor 50 are connected to a fluid supply tube 76, which connects to working channel 38 at the proximal end of endoscope 22. An electronically-controlled valve 78 is normally open while pump 48 is in operation, so that sensor 50 measures the pump outlet pressure. Periodically, however, CCU 44 commands valve 78 to close momentarily and takes a pressure reading from sensor 50, which in this case is indicative of the outlet pressure from working channel 38. This pressure reading may be used in addition to or instead of a reading by a sensor in the endoscope itself.

Additionally or alternatively, a volumetric flow rate sensor may be connected to tube 76.

Figure 5:
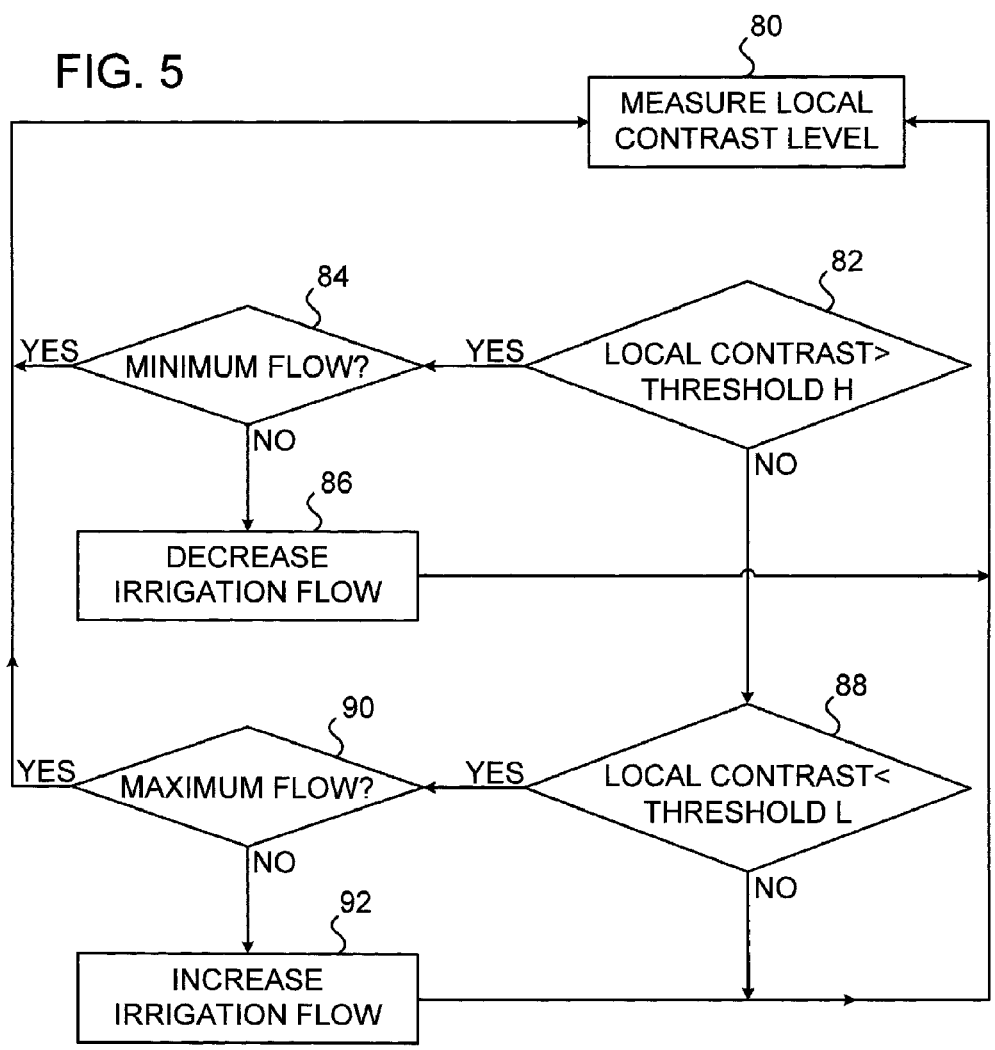
FIG. 5 is a flow chart that schematically illustrates a method for flow control, in accordance with an embodiment of the present inventive subject matter.

FIG. 5 is a flow chart that schematically illustrates a method for flow control, in accordance with an embodiment of the present inventive subject matter. The method is described herein, for the sake of clarity, with reference to the elements of system 20 that are shown and described above. Alternatively, however, the method may be implemented in substantially any endoscopic system with appropriate components for making flow and image quality measurements.

At each cycle of the method, CCU 44 makes a measurement of image quality, at a quality measurement step 80. In the present embodiment, the measure is based on the local contrast level in the image. A measure of contrast may be derived, for example, as follows:
Divide the image into 8×8 blocks.
For each block calculate the difference between the maximum pixel intensity and the minimum pixel intensity.
Average the result over all the 8×8 blocks. This is the local contrast value.
Alternatively or additionally, the CCU may derive other measures of contrast, as well as other types of image quality measures that are known in the art.

CCU 44 compares the contrast measurement to a preset upper threshold H, at an high contrast checking step 82. If the contrast is above the threshold, meaning that the picture is relatively sharp, the CCU checks the irrigation flow rate, at a low flow checking step 84. If the flow is above a preset minimum value, the CCU instructs pump 48 to decrease the flow rate by a predetermined increment, at a flow reduction step 86. The purpose of this step is to reduce the flow to the lowest rate that will maintain high image quality, thereby reducing unnecessary fluid loading of the patient's body. If the pump is already set to the minimum flow rate, the rate remains unchanged. In either case, the method returns to step 80.

On the other hand, if CCU 44 determines at step 82 that the measured contrast is below the upper threshold, it proceeds to check whether the contrast is below a preset lower threshold L, at a low contrast checking step 88. If the contrast is below the threshold, meaning that the picture is relatively blurry, the CCU checks the irrigation flow rate, at a high flow checking step 90. If the flow is below a preset maximum value, the CCU instructs pump 48 to increase the flow rate by a predetermined increment, at a flow increase step 92, so as to more effectively clear the target region of blood and debris. If the pump is already set to the maximum flow rate, the rate remains unchanged. The method then returns to step 80, and the cycle repeats.

It will be appreciated that the embodiments described above are cited by way of example, and that the present inventive subject matter is not limited to what has been particularly shown and described hereinabove. Rather, the scope of the present inventive subject matter includes both combinations and subcombinations of the various features described hereinabove, as well as variations and modifications thereof which would occur to persons skilled in the art upon reading the foregoing description and which are not disclosed in the prior art.

What is claimed is:

1. Medical apparatus, comprising: an endoscope, comprising an insertion tube, having a proximal end and a distal end, which is configured for insertion into a body cavity of a subject, and containing a working channel, which conveys a liquid from the proximal end to a target region in the body cavity adjacent to the distal end; a fluid sensor, contained in the distal end of the endoscope, which measures a rate of flow of the liquid in the working channel; and a control unit which is configured to regulate the flow of the liquid in the working channel responsively to the measured rate of flow; wherein the working channel has a segment adjacent to the distal end of the endoscope that is narrowed, a converging segment proximal to the narrowed segment, and a diverging segment distal to the narrowed segment, thus defining a Venturi tube; wherein the diameter of the converging segment narrows from about 2.5 times greater than the diameter of the narrowed segment to about the same diameter as the narrowed segment; wherein the diameter of the diverging segment expands from about the same diameter as the narrowed segment to about 3 times greater than the diameter of the narrowed segment; and the liquid exits the working channel in a divergent cone to irrigate the entire target region such that it clears blood and/or debris.

2. The apparatus according to claim 1, wherein the endoscope comprises an optical assembly contained in the distal end and configured to form an image of the target region, and wherein the control unit is configured to process the image and to regulate the flow of the fluid through the working channel responsively to a quality of the image.

3. The apparatus according to claim 2, wherein the control unit is configured to set the flow automatically, responsively to the rate of flow and the quality of the image, so as to maximize a contrast of the image while minimizing a rate of the flow, within respective, predetermined upper and lower limits of the rate and contrast.

4. A method for medical treatment, comprising:
providing an endoscope having a distal end for insertion into a body cavity of a subject and containing a working channel for conveying a liquid from a proximal end of the endoscope to a target region in the body cavity adjacent to the distal end; measuring a rate of flow of the liquid in the working channel, wherein measuring the rate of the flow comprises receiving a reading from a fluid sensor contained in the distal end of the endoscope; and regulating the flow of the liquid in the working channel responsively to the measured rate of flow; wherein the working channel has a segment adjacent to the distal end of the endoscope that is narrowed, a converging segment proximal to the narrowed segment and a diverging segment distal to the narrowed segment thus defining a Venturi tube; wherein the diameter of the converging segment narrows from about 2.5 times greater than the diameter of the narrowed segment to about the same diameter as the narrowed segment; wherein the diameter of the diverging segment expands from about the same diameter as the narrowed segment to about 3 times greater than the diameter of the narrowed segment; and the liquid exits the working channel in a divergent cone to irrigate the entire target region such that it clears blood and/or debris.

5. The method according to claim 4, wherein the endoscope comprises an optical assembly contained in the distal end and configured to form an image of the target region, and wherein regulating the flow comprises measuring a quality of the image and regulating the flow of the liquid through the working channel responsively to the measured quality of the image.

6. The method according to claim 5, wherein regulating the flow comprises setting the flow automatically, responsively to the rate of flow and the measured quality, so as to maximize a contrast of the image while minimizing a rate of the flow, within respective, predetermined upper and lower limits of the rate and contrast.

7. Medical apparatus, comprising:
an endoscope, comprising an insertion tube, having a proximal end and a distal end, which is configured for insertion into a body cavity of a subject, and containing a working channel, which conveys a liquid from the proximal end to a target region in the body cavity adjacent to the distal end; a fluid sensor, which measures a rate of flow of the liquid in the working channel; and a control unit, which is configured to regulate the flow of the liquid in the working channel responsively to the measured rate of flow;
wherein the fluid sensor is contained in the distal end of the endoscope;
the working channel ends in a nozzle at the distal end;
the nozzle includes a narrowed segment adjacent to the distal end;
the liquid exits the working channel in a divergent cone to irrigate the entire region such that it clears blood and/or debris; and
the insertion tube has a diameter about equal to or about less than 3 mm.

8. The apparatus according to claim 7, wherein the endoscope comprises an optical assembly contained in the distal end and configured to form an image of the target region, and wherein the control unit is configured to process the image and to regulate the flow of the liquid through the working channel responsively to a quality of the image.

9. The apparatus according to claim 8, wherein the control unit is configured to set the flow automatically, responsively to the rate of flow and the quality of the image, so as to maximize a contrast of the image while minimizing the rate of the flow, within respective, predetermined upper and lower limits of the rate and contrast.

* * * * *